(12) United States Patent
Zarkh

(10) Patent No.: US 12,048,492 B2
(45) Date of Patent: *Jul. 30, 2024

(54) ESTIMATING THE ENDOLUMINAL PATH OF AN ENDOLUMINAL DEVICE ALONG A LUMEN

(71) Applicant: SYNC-RX, LTD, Netanya (IL)

(72) Inventor: Michael Zarkh, Qiryat Ono (IL)

(73) Assignee: SYNC-RX LTD., Netanya (IL)

( * ) Notice: Subject to any disclaimer, the term of this patent is extended or adjusted under 35 U.S.C. 154(b) by 301 days.

This patent is subject to a terminal disclaimer.

(21) Appl. No.: 17/553,548

(22) Filed: Dec. 16, 2021

(65) Prior Publication Data

US 2022/0104888 A1    Apr. 7, 2022

Related U.S. Application Data

(63) Continuation of application No. 15/630,482, filed on Jun. 22, 2017, now Pat. No. 11,202,679.

(Continued)

(51) Int. Cl.
*A61B 34/20* (2016.01)
*A61B 5/00* (2006.01)
(Continued)

(52) U.S. Cl.
CPC ............ *A61B 34/20* (2016.02); *A61B 5/6852* (2013.01); *A61B 6/12* (2013.01); *A61B 6/487* (2013.01); *A61B 6/5241* (2013.01); *A61B 8/12* (2013.01); *A61M 25/0108* (2013.01); *A61M 25/09* (2013.01); *G06T 7/0016* (2013.01);

*G06T 7/13* (2017.01); *G06T 7/20* (2013.01); *G06T 7/30* (2017.01); *G06T 7/74* (2017.01);
(Continued)

(58) Field of Classification Search
CPC ......... A61B 34/20; A61B 5/6852; A61B 6/12; A61B 6/487; A61B 6/5241; A61B 8/12; A61B 2034/2065; A61B 2090/3966; A61B 8/4245; A61B 2560/0487; G06T 7/74; G06T 7/30; G06T 7/0016; G06T 7/20; G06T 2207/30096; G06T 2207/30101; G06T 2207/30172; G06T 2207/30241; A61M 25/0108; A61M 25/09

See application file for complete search history.

(56) References Cited

U.S. PATENT DOCUMENTS 6,148,095 A * 11/2000 Prause .................. A61B 6/504
                                                600/467
8,229,186 B2 * 7/2012 Milstein ................... G06T 7/12
                                                382/128

(Continued)

FOREIGN PATENT DOCUMENTS

WO   2008107905 A2   9/2008
WO   2009153794 A1   12/2009
(Continued)

*Primary Examiner* — Sean A Frith

(57) ABSTRACT

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

15 Claims, 7 Drawing Sheets

Related U.S. Application Data

(60) Provisional application No. 62/353,205, filed on Jun. 22, 2016.

(51) Int. Cl.

| | |
|---|---|
| *A61B 6/00* | (2024.01) |
| *A61B 6/12* | (2006.01) |
| *A61B 8/00* | (2006.01) |
| *A61B 8/12* | (2006.01) |
| *A61B 90/00* | (2016.01) |
| *A61M 25/01* | (2006.01) |
| *A61M 25/09* | (2006.01) |
| *G06T 7/00* | (2017.01) |
| *G06T 7/13* | (2017.01) |
| *G06T 7/20* | (2017.01) |
| *G06T 7/30* | (2017.01) |
| *G06T 7/73* | (2017.01) |

(52) U.S. Cl.
CPC ..... *A61B 8/4245* (2013.01); *A61B 2034/2065* (2016.02); *A61B 2090/3966* (2016.02); *A61B 2560/0487* (2013.01); *G06T 2207/30096* (2013.01); *G06T 2207/30101* (2013.01); *G06T 2207/30104* (2013.01); *G06T 2207/30172* (2013.01); *G06T 2207/30241* (2013.01)

(56) References Cited

U.S. PATENT DOCUMENTS

| | | | |
|---|---|---|---|
| 8,634,627 B2 * | 1/2014 | Fujisawa | ............... A61B 6/504 378/4 |
| 8,700,130 B2 | 4/2014 | Iddan | |
| 8,781,193 B2 | 7/2014 | Steinberg | |
| 10,172,582 B2 | 1/2019 | Dascal | |
| 11,202,679 B2 * | 12/2021 | Zarkh | ....................... G06T 7/20 |
| 2008/0221440 A1 | 9/2008 | Iddan | |
| 2010/0222671 A1 | 9/2010 | Cohen | |
| 2011/0026793 A1 * | 2/2011 | Goel | ........................ G06T 7/60 382/131 |
| 2012/0004537 A1 | 1/2012 | Tolkowsky | |
| 2012/0230565 A1 | 9/2012 | Steinberg | |
| 2013/0223702 A1 * | 8/2013 | Holsing | ................... A61B 6/12 382/128 |
| 2014/0094691 A1 | 4/2014 | Steinberg | |
| 2014/0121513 A1 | 5/2014 | Tolkowsky | |
| 2014/0140597 A1 | 5/2014 | Barzelay | |
| 2014/0270436 A1 * | 9/2014 | Dascal | ................. A61B 5/0073 382/130 |
| 2015/0342551 A1 | 12/2015 | Lavi | |
| 2016/0157805 A1 | 6/2016 | Bathina | |
| 2016/0335766 A1 | 11/2016 | Ambwani | |

FOREIGN PATENT DOCUMENTS

| | | | | |
|---|---|---|---|---|
| WO | 2010058398 A2 | 5/2010 | | |
| WO | 2011145094 A2 | 11/2011 | | |
| WO | 2012014212 A2 | 2/2012 | | |
| WO | 20120176191 A1 | 12/2012 | | |
| WO | 2013175472 A2 | 11/2013 | | |
| WO | 2014002095 A2 | 1/2014 | | |
| WO | 2014124447 A1 | 8/2014 | | |
| WO | WO-2014124447 A1 * | 8/2014 | ............ A61B 5/065 | |
| WO | 20150155770 A1 | 10/2015 | | |
| WO | 2015173821 A1 | 11/2015 | | |

* cited by examiner

ESTIMATING THE ENDOLUMINAL PATH OF AN ENDOLUMINAL DEVICE ALONG A LUMEN

CROSS-REFERENCE TO PRIOR APPLICATIONS

This application is a continuation of U.S. patent application Ser. No. 15/630,482, filed on Jun. 22, 2017, now U.S. Pat. No. 11,202,679, which claims the benefit of U.S. Provisional Patent Application 62/353,205, filed Jun. 22, 2016, each of which is hereby incorporated by reference herein.

FIELD OF EMBODIMENTS OF THE INVENTION

Some applications of the present invention generally relate to automatic image processing. Specifically, some applications of the present invention relate to medical imaging and analysis of such images.

BACKGROUND

Medical imaging is used to treat and diagnose diseases. There are a large number of imaging modalities that are used to generate medical images, including video, fluoroscopy, angiography, ultrasound, CT, MR, PET, PET-CT, CT angiography, SPECT, Gamma camera imaging, Optical Coherence Tomography (OCT), Near-Infra-Red Spectroscopy (NIRS), Vibration Response Imaging (VRI), optical imaging, infrared imaging, electrical mapping imaging, other forms of functional imaging. Focused Acoustic Computed Tomography (FACT), Optical Frequency Domain Imaging (OFDI).

There are a large variety of endoluminal medical devices that are used both for therapeutic and diagnostic purposes. Devices such as intravascular ultrasound (IVUS) probes, fractional flow reserve (FFR), and instantaneous wave-free ratio (iFR) probes typically acquire endoluminal data while moving through a lumen.

SUMMARY OF EMBODIMENTS

In accordance with some applications of the present invention, an endoluminal device that includes one or more radiopaque portions moves through a lumen of a subject. Typically, the lumen is a blood vessel that moves as a result of the subject's cardiac cycle, respiratory cycle, and/or large body movement of the subject. For example, the blood vessel may be a coronary artery. Using a radiographic imaging device, a sequence of radiographic images of a portion of the subject's body in which the lumen is disposed is acquired, during movement of the endoluminal device through the lumen. For example, the endoluminal device may be an endoluminal data-acquisition device that acquires data from inside the lumen while the device is moved along the lumen, e.g., an endoluminal imaging device, such as an IVUS probe.

A computer processor identifies locations at which the one or more radiopaque portions of the endoluminal device were imaged during the movement of the endoluminal device through the lumen, by analyzing the sequence of radiographic images. The computer processor defines a set of locations at which the one or more radiopaque portions of the endoluminal device were disposed during the movement of the endoluminal device through the lumen, based upon the identified locations.

For example, a combined image may be generated in which the identified locations form an integrated set of locations, by overlaying, upon each other, images in which the radiopaque portions of the endoluminal device have been identified. An endoluminal path of the device through the lumen is estimated based upon the set of locations. Typically, a curve that defines the set of locations is identified and the endoluminal path of the device through the lumen is determined based upon the curve. An output is generated on an output device, based upon the estimated endoluminal path of the device along the lumen.

The present invention will be more fully understood from the following detailed description of embodiments thereof, taken together with the drawings, in which:

DETAILED DESCRIPTION OF EMBODIMENTS

Figure 1:
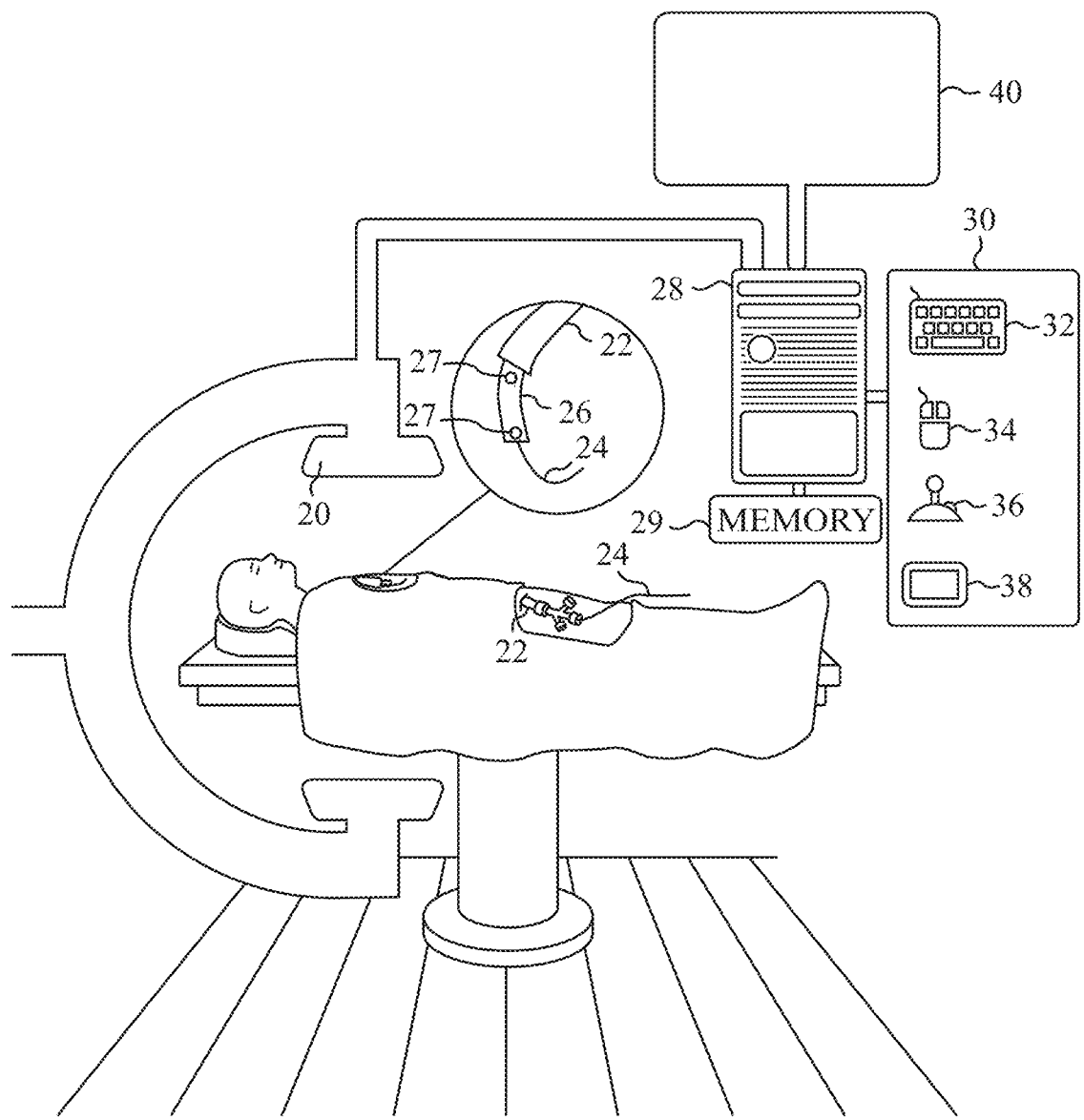
FIG. 1 is a schematic illustration of apparatus that is used in a catheterization laboratory, in accordance with some applications of the present invention.

Reference is now made to FIG. 1, which is a schematic illustration of apparatus that is used in a catheterization laboratory, in accordance with some applications of the present invention. Typically, a subject is imaged using an extraluminal imaging device (i.e., an extraluminal image-acquisition device) 20, which may include a fluoroscope that acquires fluoroscopic images in the absence of contrast agent in the blood vessels of the subject that are being imaged) and/or in angiographic mode, while there is a presence of contrast agent in the blood vessels of the subject that are being imaged.

FIG. 1 additionally shows a guide catheter 22 that has been inserted into a lumen of the subject (e.g., a blood vessel, such as a coronary artery) over a guidewire 24. An endoluminal device 26 has been inserted into the subject's lumen (e.g., the subject's blood vessel, such as the subject's coronary artery), through the guide catheter and over the guidewire. Typically, the endoluminal device includes radiopaque portions 27 (e.g., radiopaque markers). For some applications (e.g., for applications in which the endoluminal device is an iFR probe), the endoluminal device is inserted into the vessel in the absence of guidewire 24.

For some applications, endoluminal device 26 includes an endoluminal data-acquisition device that is configured to acquire data (e.g., functional data or images) from inside the subject's blood vessels. For some applications, the endoluminal data-acquisition device is an imaging probe, such as an IVUS probe. For some applications, the endoluminal data-acquisition device is a probe that acquires data in a form other than images, such as an FFR probe, and/or an iFR probe. For example, the data may include data related to pressure, flow, temperature, electrical activity, oxygenation, biochemical composition, or any combination thereof.

For some applications, endoluminal device 26 includes a therapeutic device, such as a stent, a balloon (e.g., an angioplasty balloon), a graft, a filter, a valve, and/or a different type of therapeutic endoluminal device.

A computer processor 28 typically receives and processes images (e.g., extraluminal images or endoluminal images). The computer processor communicates with a memory 29. Via a user interface 30, a user (e.g., a physician and/or a catheterization laboratory technician) sends instructions to the computer processor. For some applications, the user interface includes a keyboard 32, a mouse 34, a joystick 36, a touchscreen device 38 (such as a smartphone or a tablet computer), a touchpad, a trackball, a voice-command interface, and/or other types of user interfaces that are known in the art. Typically, the computer processor generates an output using an output device 40. Further typically, the output device includes a display, such as a monitor (as shown in FIG. 1), and the output includes an output that is displayed on the display. For some applications, the display includes a head-up display and/or a head-mounted display, such as Google Glass®. For some applications, the processor generates an output on a different type of visual, text, graphics, tactile, audio, and/or video output device, e.g., speakers, headphones, a smartphone, or a tablet computer. For some applications, user interface 30 acts as both an input device and an output device. For some applications, the processor generates an output on a computer-readable medium (e.g., a non-transitory computer-readable medium), such as a disk, or a portable USB drive.

It is noted that, for some applications, more than one computer processor is used to perform the functions described herein as being performed by computer processor 28. For some applications, more than one extraluminal imaging device is used with computer processor 28. For example, a first extraluminal imaging device may be used to acquire a first set of extraluminal images, and a second extraluminal imaging device may be used to acquire a second set of extraluminal images.

Figure 2A:
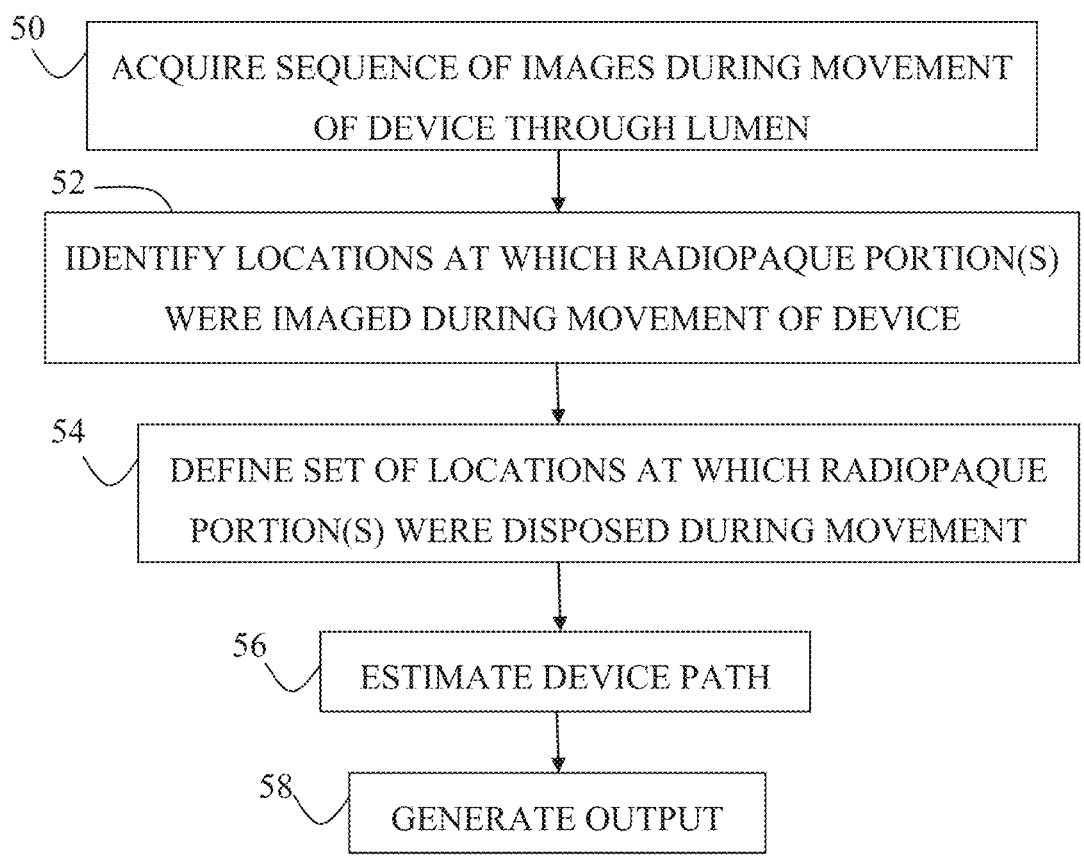
FIGS. 2A and 2B are flowcharts showing steps of an algorithm that is performed by a processor, in accordance with some applications of the present invention.
Figure 2B:
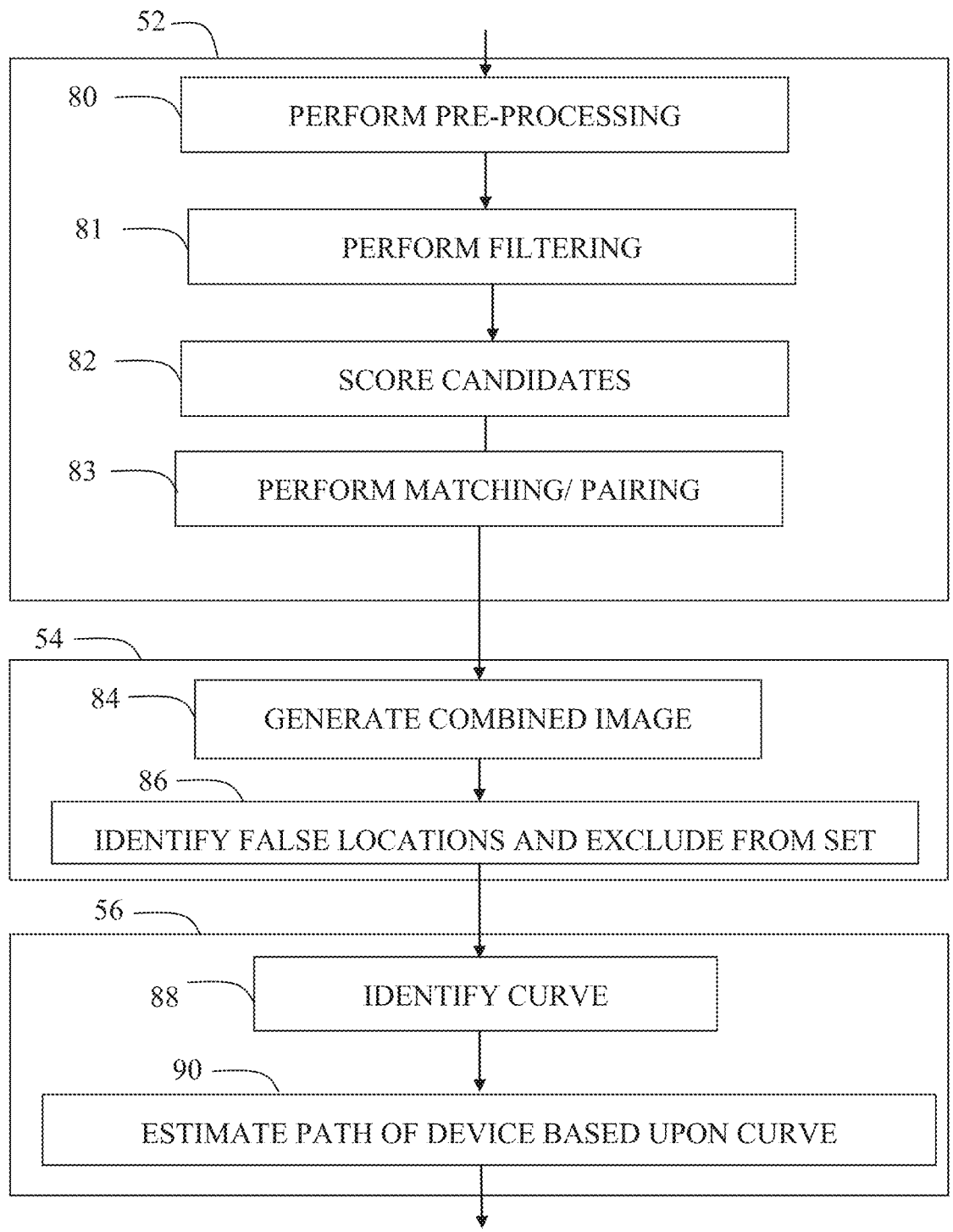

Reference is now made to FIGS. 2A-B, which are flowcharts showing steps of an algorithm that is performed, in accordance with some applications of the present invention. FIG. 2A shows a general algorithm that is performed in accordance with some applications of the invention, and FIG. 2B shows sub-steps that are performed within some of the steps of the algorithm that is shown in FIG. 2A.

For some applications, endoluminal device 26 is moved along a lumen, such as a blood vessel. For example, the endoluminal device may move through the lumen by being pushed forward through the lumen, or pulled back through the lumen. Typically, endoluminal device 26 is moved along a moving blood vessel. For example, the blood vessel may undergo motion due to the subject's cardiac cycle, due the subject's respiratory cycle, due to large body motion of the subject, and/or due the movement of device 26 along the blood vessel (e.g., due to the device changing the shape of the portion of the vessel in which it is disposed). For some applications, the blood vessel is a coronary artery. For some applications, endoluminal device 26 is an endoluminal data-acquisition device, such as an IVUS probe, that is configured to acquire respective data sets from inside the blood vessel, at respective locations along the blood vessel, while the device is moved along the blood vessel. For example, the data set that is acquired at each of the locations along the blood vessel may be an image that is acquired at the location, and/or a data set that is acquired at the location that is indicative of a functional characteristic of the blood vessel at the location (i.e., a functional data set).

With reference to FIG. 2A, in a first step 50, a sequence of radiographic images is acquired during the movement of endoluminal device 26 through the blood vessel. For some applications, the sequence of images is a sequence of fluoroscopic images that is acquired in the absence of contrast agent in the blood vessel. Due to the absence of contrast agent in the blood vessel, the blood vessel itself is substantially not visible within the images, but the radiopaque portions 27 of endoluminal device 26 are visible within the images. In addition, other radiopaque features, e.g., anatomical features (such as the subject's ribs), and/or non-anatomical features (such as CABG clips or wires), may be visible within images belonging to the radiographic image sequence. It is noted that, for some applications, contrast agent is periodically injected into the blood vessel, while the sequence of images is acquired.

In a second step 52, computer processor 28 identifies locations at which radiopaque portion(s) 27 of endoluminal device 26 were imaged in images belonging to the sequence, by analyzing images belonging to the radiographic image sequence.

Referring to FIG. 2B, for some applications, step 52 is performed using the following algorithm. In a first sub-step 80, the computer processor performs pre-processing upon the images belonging to the sequence of images. For example, the pre-processing may include the reduction of static and/or dynamic noise, background removal, background normalization, or a combination thereof. For some applications, the preprocessing includes the detection and removal from the image frames of coronary artery bypass grafting (CABG) wires, CABG clips, wires and/or electrodes of implanted tools such as pacemakers or defibrillators, and/or wires and/or electrodes of external devices such as an ECG monitor, and/or an external defibrillator.

In a second sub-step 81, the computer processor performs filtering in order to emphasize portions of the image that are candidates for radiopaque portions of the endoluminal device.

In a third sub-step 82, candidates for radiopaque portions of the endoluminal device are scored, based on the extent to which the candidates exhibit characteristics of the radiopaque portions.

In a fourth sub-step 83, it is determined whether candidates having a score that passes a threshold score can be matched or paired to each other based upon relative location, distance, orientation, visual similarity, and/or other factors. Candidates that satisfy a matching and/or pairing criterion are identified as corresponding to the radiopaque portions of the tool.

It is noted that, as described hereinbelow with reference to step 86 and with reference to FIGS. 3A-C, some visible elements may falsely be identified as corresponding to radiopaque portions of the endoluminal device. Typically, step 86 is performed, in order to account for such elements.

For some applications, the computer processor uses machine-learning techniques in order to identify radiopaque portions of the device, if the radiopaque portions of the device have a given machine-learnable characteristic (e.g., a given shape, or pattern).

For some applications, the radiopaque portion(s) of the endoluminal device include radiopaque markers and the markers are identified using one or more of the techniques described in U.S. Pat. No. 8,781,193 to Steinberg, which is incorporated herein by reference. For some applications, the radiopaque portion(s) of the endoluminal device include an elongate radiopaque element (e.g., the radiopaque tip of a guidewire). Such an element may be detected by detecting a set of pixels with high maximal eigenvalue and low absolute value of low eigenvalue. For some applications, the radiopaque portion(s) of the endoluminal device are identified using techniques for identifying an object in an image as described in International Patent Application PCT/IL2015/050509 to Klaiman (published as WO 15/173821), which is incorporated herein by reference.

For some applications, radiopaque markers and/or elongate radiopaque elements are identified using one or more of the following steps:

a. Pre-processing: Individual image frames (or a region of interest (ROI) within such frames) along the image sequence are pre-processed in order to facilitate the subsequent identification of markers. Such pre-processing typically comprises the reduction of static and/or dynamic noise, background removal, or a combination thereof. For some applications, a median filter, a Mexican hat filter, a directional Mexican hat filter, and/or a low-pass filter is applied to the individual image frames. For some applications, the preprocessing includes the detection and removal from the image frames of CABG wires, CABG clips, wires and/or electrodes of implanted tools such as pacemakers or defibrillators, and/or wires and/or electrodes of external devices such as an ECG monitor, and/or an external defibrillator.

b. Filtering of non-marker-like features: Individual image frames (or an ROI within such frames) along the image sequence are processed to filter out remaining features that are clearly not markers. For some applications, the filtering includes the application to the image frames of a median filter, a Mexican hat filter, a directional Mexican hat filter, a maximal stable external regions (MSER) filter, an MSER-like filter, a Hessian filter, or a combination thereof.

For some applications, Hessian eigenvalues are calculated for each pixel in each image frame, or for all pixels within an ROI of the image frame. Typically, local clusters of pixels with high minimal eigenvalues represent a "paraboloid-like" area in the image and are identified as a potential radiopaque marker.

c. Scoring: Remaining features in individual image frames (or an ROI within such frames) along the image sequence are assigned a "fitness" score (i.e., a "markerness" score, or a "dotness" score in the case of the most common markers), describing the likelihood that they are markers. For some applications, the score is calculated from the abovementioned filtering.

d. Matching: Remaining features in individual image frames (or an ROI within such frames) are analyzed for matching with one another. For example, in the case of aiming to detect the two radiopaque markers of an endoluminal device, pair-matching is performed. Such matching is typically performed based upon relative location, distance, orientation, visual similarity, and/or other factors.

e. Detection: For some applications, once a pair of clusters (with such two clusters being strong candidates to be tool markers) has been identified at a similar distance from one another and/or relative angle to one another in several consecutive image frames, the pair of clusters is determined to be the two markers of a tool.

f. Bridging: For some applications, if two elongate elements are detected, the computer processor determines whether the ends of the elements match one another, based upon the locations of the elements and the orientations of the ends of the elements. Matched ends are connected by a straight line, such that the two elements are combined into a single elongate element.

Typically, the output of performing step 52 of FIG. 2A is that a set of binary images is generated, in which, in each of the images belonging to the set, pixels that have been identified as corresponding to the radiopaque portions of the endoluminal device are assigned a first value, and pixels that have not been identified as corresponding to the radiopaque portions of the endoluminal device have a second value.

Referring again to FIG. 2A, in a third step 54, the computer processor defines a set of locations at which the one or more radiopaque portions of the endoluminal device were disposed during the movement of the endoluminal device through the lumen, based upon the identified locations. As shown in FIG. 2B, for some applications, the third step is performed using by first performing a sub-step 84 of generating a combined image, by overlaying, upon each other, the binary images generated in step 52.

Figure 3A:
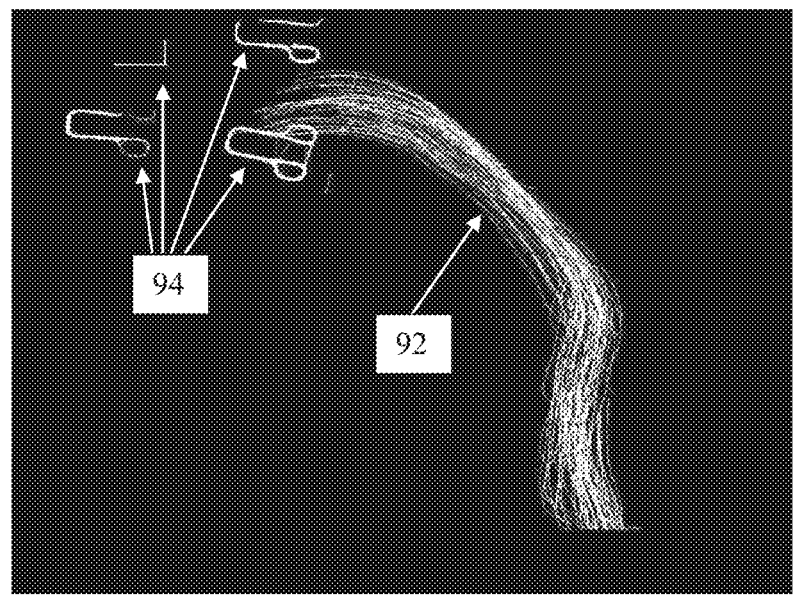
FIG. 3A is an example of a combined image that is generated by overlaying a plurality of binary images upon one another, in accordance with some applications of the present invention.
Figure 3B:
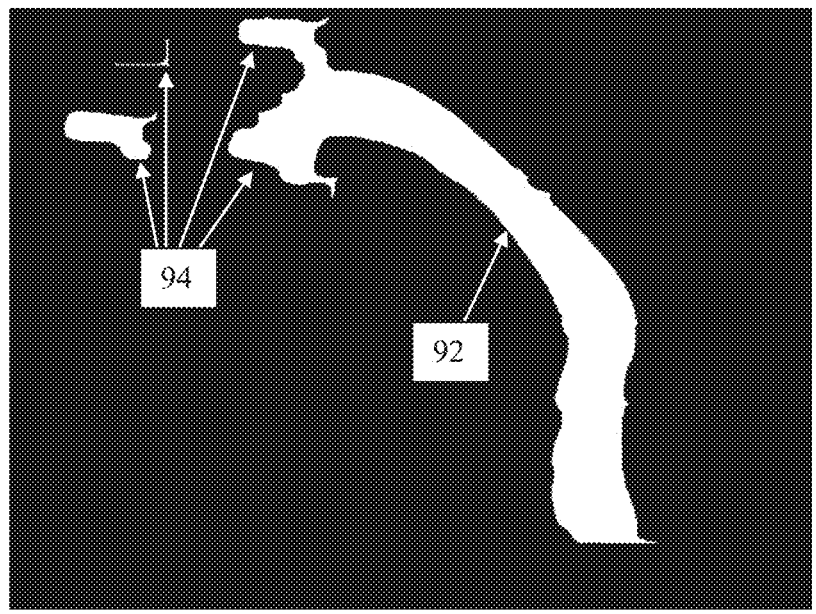
FIGS. 3B and 3C are examples of images that are generated by applying image-processing techniques to the combined image of FIG. 3A, in order to identify locations of a radiopaque portion of the endoluminal device in the combined image shown in FIG. 3A, in accordance with some applications of the present invention.

Reference is now made to FIGS. 3A and 3B, which are examples of a combined image (FIG. 3A) that was generated by overlaying a plurality of binary images upon one another, and an image (FIG. 3B) generated by performing morphological operations upon the combined image, in accordance with some applications of the present invention.

FIG. 3A was generated by acquiring a sequence of radiographic images of a human subject's coronary arteries, while a guidewire having a radiopaque tip was pulled-back through the coronary artery. Binary images were generated, based upon images belonging to the sequence, and the binary images were then overlaid upon each other, in the manner described hereinabove. As shown, the set of locations at which visible elements that were identified as corresponding to the locations at which the radiopaque tip of the guidewire were imaged is the white portion of the combined image. FIG. 3B was generated by performing closure upon the set of locations at which the radiopaque tip of the guidewire were imaged, within the combined image shown in FIG. 3A, in accordance with some applications of the present invention.

For some applications, the blood vessel undergoes cyclical motion as a result of a physiological cycle of the subject (such as the subject's cardiac cycle, or respiratory cycle). For some such applications, the computer processor performs step 54 of FIG. 2A (i.e., defining the set of locations) by defining a set of locations at which the one or more radiopaque portions of the endoluminal device were imaged at a given phase of the subject's physiological cycle. For example, the computer processor may receive the subject's ECG signal, and, using the ECG signal, the computer processor may determine locations at which the radiopaque portion(s) of the endoluminal device were determined to have been disposed at a given phase of the cardiac cycle.

For some applications, the computer processor performs step 54 of FIG. 2A (i.e., defining the set of locations) by identifying a sub-set of identified locations of the radiopaque portion(s) of the endoluminal device, such that each member of the sub-set of identified locations is disposed within a given distance of at least one other member of the sub-set of identified locations. For example, a sub-set of identified locations may be identified such that each of the members of the sub-set overlaps with at least one other member of the subset, and/or is within a given number of pixels of at least one other member of the sub-set. The computer processor then identifies the sub-set as being the set of locations at which the one or more radiopaque portions of the endoluminal device were disposed during the movement of the endoluminal device through the lumen.

As noted hereinabove, in step 52 of FIG. 2A, some visible elements may falsely be identified as corresponding to radiopaque portions of the endoluminal device. For example, in FIG. 3A (which shows the combined image before morphological operations have been applied), and in FIG. 3B (which shows the combined image after closure has been applied), in addition to white portion 92, which has a generally luminal shape, there are other white portions 94, which correspond to other visible features (such as CABG clips or wires) that are present in images belonging to the radiographic image sequence. Typically, sub-step 86 of step 54 is performed, in order to account for such elements.

In sub-step 86, the computer processor distinguishes between true and false locations at which the radiopaque portion(s) of the endoluminal device were identified within the combined image. Typically, the computer processor identifies that one or more locations within the combined image at which radiopaque features were imaged within the radiographic image sequence do not correspond to locations at which the radiopaque portions of the endoluminal device were disposed, and excludes the one or more locations from the set of locations.

For some applications, the computer processor analyzes the sequence of radiographic images in order to identify visible features that (a) undergo movement over the course of the radiographic image sequence, and (b) the movement of which includes a substantial non-cyclical component. The device moves along the blood vessel over the course of the radiographic image sequence, whereas other moving visible elements may be expected to move substantially only as a result of cyclical motion of the subject's body (e.g., as a result of the subject's cardiac cycle, or respiratory cycle). Therefore, the processor identifies visible elements as corresponding to the radiopaque portion(s) of the endoluminal device, if the visible elements (a) undergo movement over the course of the radiographic image sequence, and (b) undergo movement that includes a substantial non-cyclical component.

Since the radiopaque portion(s) of the endoluminal device move along the lumen over the course of the radiographic image sequence, the radiopaque portion(s) of the endoluminal device may be expected to be imaged at any particular location for only a relatively small portion of the radiographic image sequence. By contrast, since other visible components (such as CABG clips or wires) within the images may be expected to remain stationary with respect to the portion of the subject's body to which they are attached, such features would be expected to remain at approximately the same location throughout the sequence of radiographic images (other than movement that the portion of the subject's body undergoes). Therefore, for some applications, for each of the locations at which radiopaque elements were identified within the sequence, the computer processor determines which of the images included a radiopaque element at the location. In this manner, the computer processor is able to distinguish between (a) imaged radiopaque elements that correspond to the radiopaque portion(s) of the endoluminal device, and (b) other imaged radiopaque elements. For example, the processor may identify a location as corresponding to a true location of the radiopaque portion(s) of the endoluminal device, by determining that a visible element was imaged at the location in less than a given percentage of the images belonging to the sequence.

Further alternatively or additionally, the computer processor may identify a set of locations at which visible elements were located over the course of the radiographic image sequence, which, when viewed as an integrated set of locations, have a luminal shape. Since the endoluminal device moved along the lumen over the course of the radiographic image sequence, such locations are identified as corresponding to true locations of the radiopaque portion(s) of the device.

Figure 3C:

Reference is now made to FIG. 3C, which shows the output of step 86 having been performed on the image shown in FIG. 3B, in accordance with some applications of the present invention. As shown, subsequent to applying step 86, only white portion 92, which has a generally luminal shape, appears in the image, whereas the other white portions (portions 94 from FIG. 3B) have been removed.

Referring again to FIG. 2A, in step 56, the computer processor uses the set of locations at which the radiopaque portion(s) of the endoluminal device were disposed to estimate the endoluminal path of the device along the blood vessel. With reference to FIG. 2B, for some applications, step 56 is performed by performing sub-step 88, of identifying a curve. The curve is derived by integrating a set of locations. For some applications, a center-line of the identified locations is identified as the curve.

As described hereinabove, for some applications, before identifying the curve, the computer processor performs morphological operations on the identified set of locations at which the radiopaque portions of the endoluminal device were imaged. For example, a closure operation may be performed upon the set of locations, and the curve may be identified based upon the closed set of locations. For some applications, a center-line of the closed set of locations is identified as the curve. In sub-step 90, the endoluminal path of the device is estimated based upon the identified curve. Typically, the endoluminal path of the device is estimated as being the curve.

As described hereinabove, for some such applications, the computer processor performs step 54 of FIG. 2A (i.e., defining the set of locations) by defining a set of locations at which the one or more radiopaque portions of the endoluminal device were imaged at a given phase of the subject's physiological cycle. For such applications, the endoluminal path of the device through the lumen is estimated based upon the set of locations. For example, a curve that defines the set of locations may be identified. For some applications, a center-line of the identified locations is identified as the curve.

Also as described hereinabove, for some applications, the computer processor performs step 54 of FIG. 2A (i.e., defining the set of locations) by identifying a sub-set of identified locations of the radiopaque portion(s) of the endoluminal device, such that each member of the sub-set of identified locations is disposed within a given distance of at least one other member of the sub-set of identified locations. For such applications, the endoluminal path of the device through the lumen is estimated based upon the identified sub-set of identified locations. For example, a curve that defines the identified sub-set of locations may be identified. For some applications, a center-line of the sub-set of locations is identified as the curve.

Figure 4:
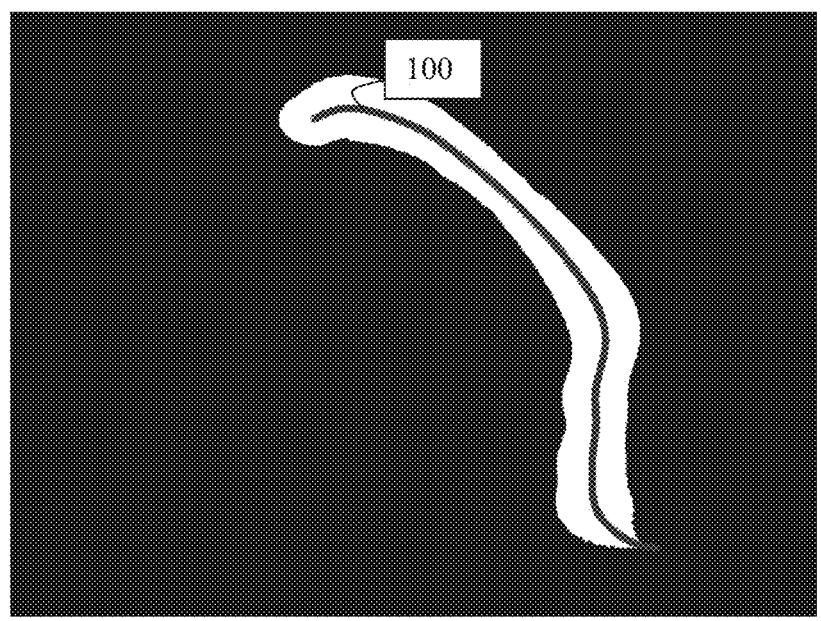
FIG. 4 is an example of an estimated endoluminal path of an endoluminal device through a lumen, the estimate being based upon locations of a radiopaque portion of the endoluminal device identified in the image shown in FIG. 3C, in accordance with some applications of the present invention.

Reference is now made to FIG. 4, which is an example of an estimated endoluminal path 100 of an endoluminal device through a lumen, the estimate being based upon the set of locations of the radiopaque portion(s) of the endoluminal device in the image shown in FIG. 3C, in accordance with some applications of the present invention. The endoluminal path shown in FIG. 4 was estimated by identifying a center-line of the closed set of locations of the radiopaque guidewire tip identified in FIG. 3C, in accordance with the techniques described hereinabove.

It is noted that, for some applications, algorithmic operations are performed by the computer processor that are the equivalent of a combined image (as shown in FIG. 3A) being generated, morphological operations being performed on the combined image (as shown in FIG. 3B), true locations of the radiopaque portion(s) of the endoluminal device being identified (as shown in FIG. 3C), and/or a curve that defines the set of locations being identified. Such algorithmic operations may be performed without images such as those shown in FIGS. 3A-C and/or without the curve as shown in FIG. 4 actually being displayed. An output may be generated by the computer processor based upon the above-described algorithmic operations being performed, in accordance with the techniques described herein.

Figure 5A:
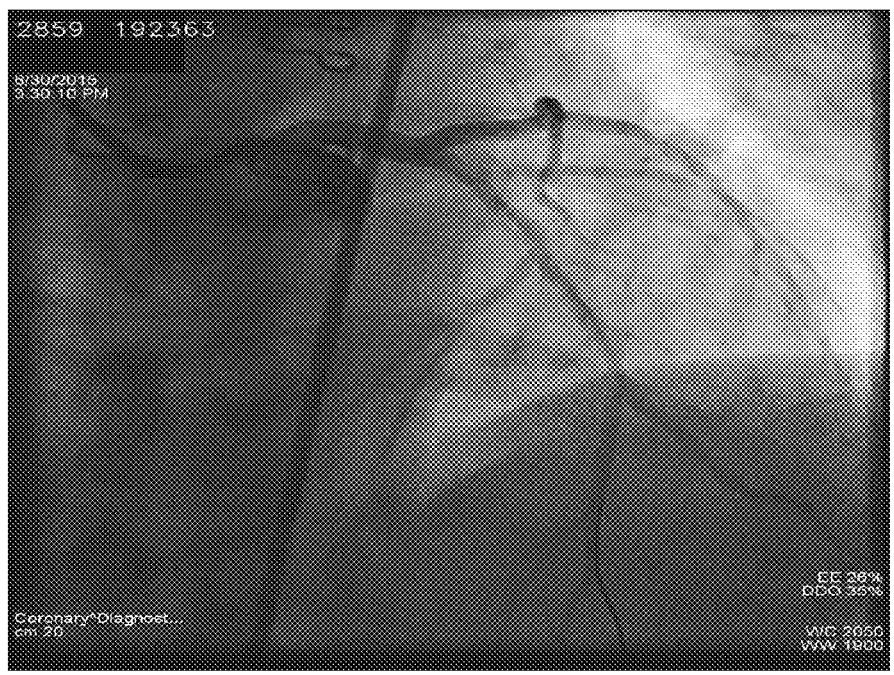
FIGS. 5A and 5B show (FIG. 5A) an angiographic image of a blood vessel, and (FIG. 5B) the angiographic image of the blood vessel, with (a) the center-line of the blood vessel, as derived manually from the angiographic image, and (b) the estimated endoluminal path of an endoluminal device through the blood vessel, both overlaid upon the angiographic image, in accordance with some applications of the present invention.
Figure 5B:
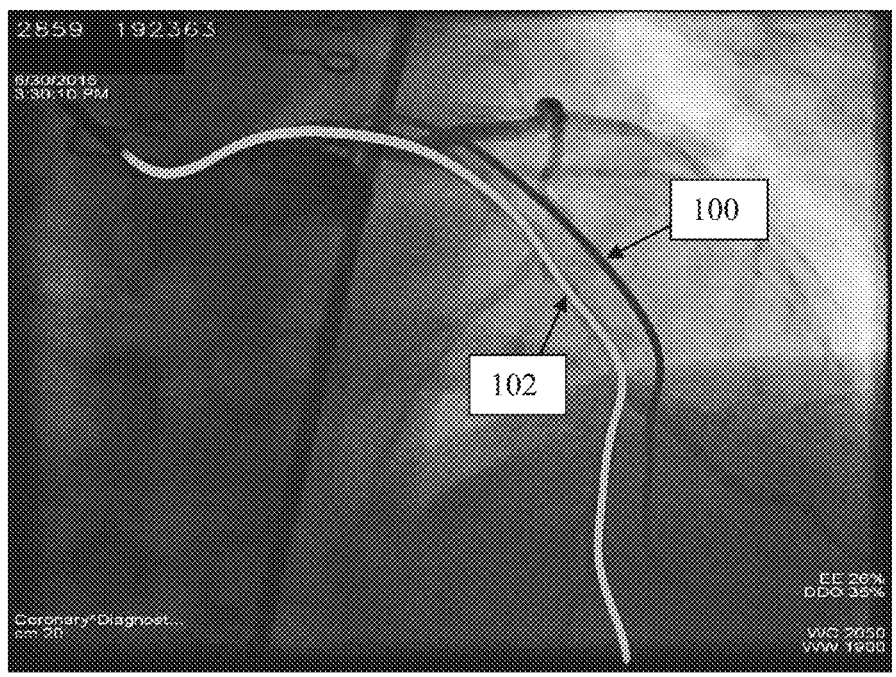
Figure 6:
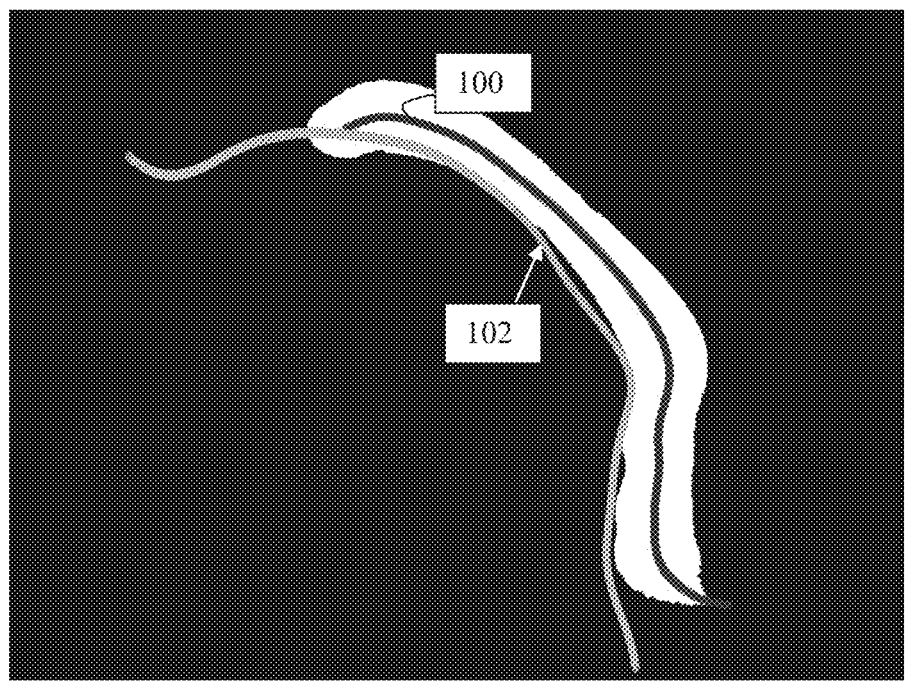
FIG. 6 shows (a) the center-line of the blood vessel, as derived manually from the angiographic image, and (b) the estimated endoluminal path of an endoluminal device through the blood vessel, both overlaid upon the image shown in FIG. 3C, in accordance with some applications of the present invention.

Reference is made to FIGS. 5A-B, which show an angiographic image of a blood vessel (FIG. 5A), and (FIG. 5B) the angiographic image of the blood vessel, with (a) a center-line 102 of the blood vessel, as derived from the angiographic image using a manual input, and (b) estimated endoluminal path 100 of an endoluminal device through the blood vessel, both overlaid upon the angiographic image, in accordance with some applications of the present invention. Reference is also made to FIG. 6, which shows (a) center-line 102 of the blood vessel, as derived from the angiographic image, and (b) estimated endoluminal path 100 of endoluminal device 26 through the blood vessel, both overlaid upon the combined and image-processed image of FIG. 3C, in accordance with some applications of the present invention.

FIG. 5A is an angiographic image of the same blood vessel as was imaged radiographically in order to generate the image shown in FIG. 3A, the angiographic image having been acquired in the presence of contrast agent inside the blood vessel, such that the blood vessel is visible in FIG. 5A. Curve 102, which is overlaid on the angiogram in FIG. 5B is the center-line of the visible vessel, as derived manually, i.e., by a user deriving the location of the center-line based upon the visible vessel. It may be observed, in both FIG. 5 and FIG. 6, that there is correspondence between the shape of center-line 102 of the blood vessel as derived from the angiographic image, and estimated endoluminal path 100 of the endoluminal device.

It is noted that path 100 was estimated for a guidewire that was moving through a coronary artery. Since coronary arteries undergo substantial movement, the endoluminal path of the guidewire along the vessel did not define a continuous curve. Nevertheless, as indicated in FIGS. 5B and 6, the path of the endoluminal device as estimated using the techniques described herein does provide a reasonable estimation of the endoluminal path along which the endoluminal device moved. Therefore, for some applications, the estimated endoluminal path is used for one or more of the techniques described herein. Referring again to FIG. 2A, typically, in a final step 58 of the procedure, an output is generated based upon the estimated endoluminal path of the endoluminal device. The output is typically generated on output device 40, e.g., a display (as shown in FIG. 1).

For some applications, computer processor 28 calibrates the estimated endoluminal path of the endoluminal device by determining the relationship between the physical length of a longitudinal portion of the blood vessel and a number of pixels in a portion of the estimated endoluminal path that corresponds to the longitudinal portion of the blood vessel (e.g., the length in mm along the blood vessel, per pixel along the estimated endoluminal path). It is noted that typically, the calibration factors associated with respective longitudinal portions of the endoluminal path of an endoluminal device in an image vary, due to respective portions of the blood vessel being disposed at respective angles with respect to the extraluminal imaging device, and, therefore, having respective amounts of foreshortening associated therewith. Therefore, typically, the computer processor determines a plurality of local calibration factors along the estimated endoluminal path, so as to determine the extent of foreshortening of respective portions of the estimated endoluminal path of the device.

For some applications, techniques are used for estimating local calibration factors along the estimated endoluminal path of the endoluminal device that are generally similar to techniques for determining local calibration factors along a roadmap pathway as described in US 2014/0094691 to Steinberg, which is incorporated herein by reference.

For some applications, the calibration is performed based upon known dimensions associated with the radiopaque portion(s) of the endoluminal device. For example, the computer processor may use the known length of a radiopaque portion of the endoluminal device, and/or a known separation between two radiopaque portions. Since the estimated endoluminal path is determined based upon the imaged radiopaque portions, the computer processor is able to determine at any given location along the endoluminal path a calibration factor associated with that location by identifying the radiopaque portion(s) within an image in which the radiopaque portion(s) appeared at that location and determining a dimension associated with the radiopaque portion(s) within the image.

For some applications, even if physical dimensions associated with the radiopaque portion(s) are not known, the computer processor determines the relative calibration factors of respective longitudinal portions of the estimated endoluminal path of the endoluminal device, based upon the relative number of pixels that a given radiopaque portion, or separation between radiopaque portions, occupies while the endoluminal device was disposed at respective locations along the estimated endoluminal path.

For some applications, a length scale is placed along the roadmap pathway of the roadmap image based upon the determined calibration factors.

As described hereinabove, for some applications, endoluminal device 26 is an endoluminal data-acquisition device that is configured to acquire respective data sets from inside the blood vessel, at respective locations along the blood vessel, while the device is moved along the blood vessel. For some applications, the endoluminal data-acquisition device is an imaging probe, such as an IVUS probe. For some applications, the endoluminal data-acquisition device is a probe that acquires data in a form other than images, such as an FFR probe, and/or an iFR probe. For example, the data may include data related to pressure, flow, temperature, electrical activity, oxygenation, biochemical composition, or any combination thereof. Thus, in accordance with some applications, the data set that is acquired at each of the locations along the blood vessel is an image that is acquired at the location, and/or a data set that is acquired at the location that indicative of a functional characteristic of the blood vessel at the location (i.e., a functional data set).

For some such applications, computer processor 28 registers respective endoluminal data sets to respective locations along the estimated endoluminal path of the device through the lumen. For example, the computer processor may determine that, when a given endoluminal data set was acquired, one of the radiographic images belonging to the sequence of radiographic images was acquired. The computer processor may derive the location of the endoluminal data set with respect to the estimated endoluminal path of the endoluminal device, based upon the location of the radiopaque portion(s) of the endoluminal device within the radiographic image.

For some applications, in the above-described manner, the computer processor coregisters respective endoluminal data sets to respective locations along the estimated endoluminal path of the endoluminal device through the lumen, without requiring the user to input an indication of the shape and/or location of the vessel lumen. For some such applications, in response to a single input from the user that is indicative of a desire of the user to perform coregistration of endoluminal data sets to the lumen path, the computer processor automatically performs the coregistration.

For some applications, computer processor 28 uses the endoluminal data sets to determine the vessel diameter at respective locations along the estimated endoluminal path of the endoluminal device. In this manner, the computer processor may, for example, identify a location of a lesion (e.g., a partial occlusion) within the blood vessel, with respect to the estimated endoluminal path of the endoluminal device, and/or may perform quantitative analysis on the blood vessel with respect to the estimated endoluminal path of the device. For some applications, the computer processor measures dimensions of an identified lesion, and a tool (e.g., a stent or an angioplasty balloon) is selected for placement at the lesion in response thereto.

Alternatively or additionally, the computer processor may generate a virtual representation of the vessel upon the display. For example, the computer processor may use the estimated endoluminal path of the endoluminal device to provide information regarding the shape of the vessel, and the derived diameters of the vessel to provide information regarding the diameters of the vessel at respective longitudinal locations along the vessel.

For some applications, the computer processor derives the location of the vessel center-line from an angiographic image of the blood vessel that is received by the computer processor. In accordance with respective applications, the angiographic image is acquired before the endoluminal device is placed within the lumen, while the endoluminal device is disposed within the lumen, or after the endoluminal device is removed from within the lumen. For example, FIG. 5 shows center-line 102 as derived from the angiographic image upon which the center-line is overlaid.

It is noted that center-line 102 was derived manually (i.e., based upon input from a user). However, for some applications, the computer processor automatically derives the location of the vessel center-line from an angiographic image of the blood vessel that is received by the computer processor. For example, the computer processor may derive the location of the vessel center-line using active contour methods, using the estimated path curve as an input. Or, the computer processor may perform optimization on a graph representing the vasculature in the image.

Alternatively or additionally, the computer processor may receive an indication from a user of the location of the vessel center-line upon an angiographic image of the vessel. For example, the computer processor may derive the location of the vessel center-line using techniques as described in U.S. Pat. No. 8,781,193 to Steinberg, which is incorporated herein by reference. For some applications, using an input device, the user indicates the location of the vessel center-line upon a displayed angiographic image. For some applications, the computer processor derives the location of the vessel center-line from an angiographic image of the blood vessel that is received by the computer processor, based upon manual input in combination with automatic image-processing steps. For example, an automatically-derived center-line may be displayed and the computer may allow the user to perform local corrections upon the automatically-derived center-line.

For some applications, the computer processor determines a transformation function for transforming the shape of the estimated endoluminal path of the endoluminal device to the shape of a vessel center-line, as derived (manually and/or automatically) from the angiographic image. For example, a transformation function may be determined using techniques as described in US 2010/0222671 to Cohen, and/or in US 2014/0094691 to Steinberg, both of which applications are incorporated herein by reference. In this manner, the computer processor registers respective locations along the estimated endoluminal path of the device through the lumen to respective locations along the center-line of the lumen within the angiographic image of the lumen.

For some applications, using the above-described transformation function, the computer processor determines a correspondence between respective longitudinal locations along the estimated endoluminal path of the endoluminal device, and respective longitudinal locations along the vessel center-line, as derived from the angiographic image. As described hereinabove, for some applications, computer processor 28 registers respective endoluminal data sets to respective locations along the estimated endoluminal path of the device through the lumen. For some such applications, in a subsequent step, the computer processor co-registers respective endoluminal data sets to respective longitudinal locations along the vessel center-line, as derived from the angiographic image. Typically, the computer processor performs the aforementioned co-registration step based upon the determined correspondence between respective longitudinal locations along the estimated endoluminal path of the endoluminal device, and respective longitudinal locations along the vessel center-line, as derived from the angiographic image. Thus, coregistration of endoluminal data sets to the vessel center-line is performed by, first coregistering respective endoluminal data sets to respective locations along the estimated endoluminal path, and then registering the estimated endoluminal path to the vessel center-line. Alternatively, the coregistration of endoluminal data sets to the vessel center-line is performed by directly coregistering respective endoluminal data sets to respective locations along the vessel center-line.

As described hereinabove, for some applications, the computer processor coregisters respective endoluminal data sets to respective locations along the estimated endoluminal path of the endoluminal device through the lumen, without requiring the user to input an indication of the shape and/or location of the path of the lumen. Alternatively or additionally, the computer processor coregisters respective endoluminal data sets to respective locations along an automatically-derived vessel center-line that is derived using the estimated endoluminal path, as described above. For some applications, in response to a single input from the user that is indicative of a desire of the user to perform coregistration of endoluminal data sets to the vessel center-line, the computer processor automatically performs the coregistration, using the coregistration techniques described herein.

For some applications, based upon the co-registering of the respective endoluminal data sets to the respective longitudinal locations along the vessel center-line, as derived from the angiographic image, the computer processor identifies a location of a lesion (e.g., a partial occlusion) within the blood vessel, with respect to the vessel center-line. For some applications, the computer processor measures dimensions of an identified lesion, and, optionally, a tool (e.g., a stent or an angioplasty balloon) is selected for placement at the lesion in response thereto.

For some applications, computer processor 28 performs quantitative analysis on the blood vessel with respect to the vessel center-line. For some applications, the computer processor generates a virtual representation of the vessel upon the display. For example, the computer processor may use the vessel center-line as derived from the angiographic image to provide information regarding the shape of the vessel, and the derived diameters of the vessel to provide information regarding the diameters of the vessel at respective longitudinal locations along the vessel center-line.

For some applications, endoluminal path 100 is identified at least partially by using, as an input, a vessel center-line as derived (manually or automatically) from an angiographic image. Typically, the vessel center-line is used in combination with the identified locations of the radiopaque portion(s) of the endoluminal device over the sequence of radiographic images. For example, the computer processor may perform a best-fit operation, to best fit the vessel center-line to the identified locations of the radiopaque portion(s) of the endoluminal device.

Figure 7:
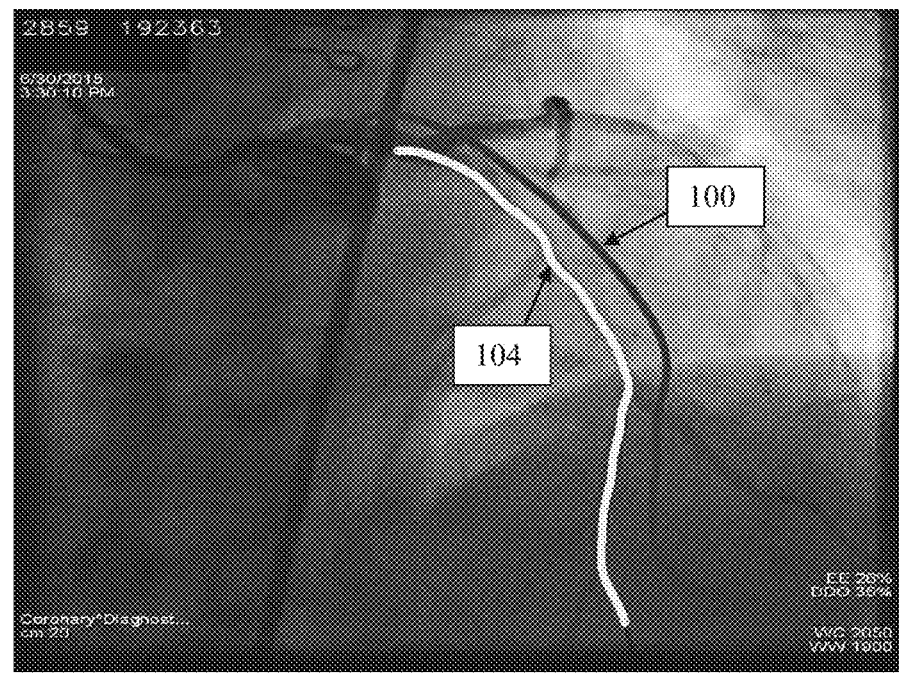
FIG. 7 shows (a) the estimated endoluminal path of an endoluminal device through the blood vessel, and (b) an estimated center-line of the vessel that was derived automatically using the estimated endoluminal path of the endoluminal device through the blood vessel, both overlaid upon an angiographic image of the blood vessel, in accordance with some applications of the present invention.

Reference is now made to FIG. 7, which shows an angiographic image of a blood vessel with (a) an estimated endoluminal path 100 of endoluminal device 26 through the blood vessel, and (b) a vessel center-line 104 automatically derived based upon estimated endoluminal path 100, both overlaid upon the angiographic image, in accordance with some applications of the present invention.

For some applications, the computer processor uses the estimated endoluminal path of the endoluminal device through the lumen as an input for determining the location of the center-line of the lumen. For example, the computer processor may receive an angiographic image of a blood vessel, and uses the estimated endoluminal path of an endoluminal device through the blood vessel as an input for determining the location of the vessel center-line with respect to the angiographic image. As noted hereinabove with reference to FIGS. 5B and 6, there is typically correspondence between the shape of the center-line of a blood vessel, and the estimated endoluminal path of an endoluminal device through the blood vessel. Therefore, for some applications, the computer processor uses the estimated endoluminal path as an input for estimating the center-line of the vessel. In this manner, the vessel center-line may be determined automatically, without requiring an input from a user. As may be observed in FIG. 7, an automatically derived center-line provides a reasonable estimate of the location of the vessel center-line.

For some applications, the above-described technique for using the estimated endoluminal path of an endoluminal device through the blood vessel as an input for determining the location of the vessel center-line with respect to the angiographic image, is applied to a plurality of angiographic images, such as to generate a plurality of angiographic images with vessel center-lines indicated thereon. For some such applications, the computer processor then selects one of the vessel center-lines to be used for additional processing steps (or to be displayed to the user), based upon the quality of the resulting center-lines. For example, in selecting the center-line, the computer processor may use criteria that include the quality of shape match between an input image and the resulting center-line, and/or the strength of a vesselness value in the image based on the resulting center-line. For some applications, the computer processor allows the user to select which center-line to use.

It is noted that although some techniques described herein are described primarily with respect to extraluminal fluoroscopic/angiographic images, the scope of the present invention includes applying the techniques described herein to other forms of extraluminal images, mutatis mutandis.

Although some techniques described herein are described primarily as being performed on an artery, the scope of the present application includes performing similar techniques on any lumen in the vascular system, the respiratory tract, the digestive tract, the urinary tract, any other luminal structure within a patient's body, or any other suitable anatomical structure within a patient's body, mutatis mutandis. Examples of an anatomical structure to which the techniques described herein may be applied include a coronary vessel, a coronary lesion, a vessel, a vascular lesion, a lumen, a luminal lesion, and/or a valve.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 28. For the purposes of this description, a computer-usable or computer-readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer-readable medium is a non-transitory computer-usable or computer-readable medium.

Examples of a computer-readable medium include a semiconductor or solid state memory, magnetic tape, a removable computer diskette, a random access memory (RAM), a read-only memory (ROM), a rigid magnetic disk, and an optical disk. Examples of optical disks include compact disk-read only memory (CD-ROM), compact disk-read/write (CD-R/W) and DVD.

A data processing system suitable for storing and/or executing program code will include at least one processor (e.g., computer processor 28) coupled directly or indirectly to memory elements (e.g., memory 29) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem, and Ethernet cards are just a few of the currently available types of network adapters.

Computer program code for carrying out operations of the present invention may be written in any combination of one or more programming languages, including an object-oriented programming language such as Java, Smalltalk, C++ or the like, and conventional procedural programming languages, such as the C programming language or similar programming languages.

It will be understood that each block of the flowcharts shown in FIGS. 2A-B and combinations of blocks in the flowchart, can be implemented by computer program instructions. These computer program instructions may be provided to a processor of a general-purpose computer, special-purpose computer, or other programmable data processing apparatus to produce a machine, such that the instructions, which execute via the processor of the computer (e.g., computer processor 28) or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture, including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowcharts and/or algorithms described in the present application.

Computer processor 28 is typically a hardware device programmed with computer program instructions to produce a special-purpose computer. For example, when programmed to perform the algorithms described with reference to FIGS. 2A-B, computer processor 28 typically acts as a special-purpose, device-path-estimation computer processor. Typically, the operations described herein that are performed by computer processor 28 transform the physical state of memory 29, which is a real physical article, to have a different magnetic polarity, electrical charge, or the like depending on the technology of the memory that is used.

There is therefore provided, in accordance with some applications of the present invention, a method for use with an endoluminal device that includes one or more radiopaque portions and that moves through a lumen of a subject, the method including:

using a radiographic imaging device, acquiring a sequence of radiographic images of a portion of the subject's body in which the lumen is disposed, during movement of the endoluminal device through the lumen; and using at least one computer processor:
identifying locations at which the one or more radiopaque portions of the endoluminal device were imaged during the movement of the endoluminal device through the lumen, by analyzing the sequence of radiographic images;
defining a set of locations at which the one or more radiopaque portions of the endoluminal device were disposed during the movement of the endoluminal device through the lumen, based upon the identified locations;
estimating an endoluminal path of the device through the lumen based upon the set of locations; and
generating an output on an output device.

In some applications, the lumen includes a lumen of the subject that undergoes motion, and estimating the endoluminal path includes estimating the endoluminal path of the device through the lumen that undergoes motion.

In some applications, the method further includes, based upon the estimated endoluminal path, registering a current position of the portion of the subject's body to an additional image of the portion of the subject's body, by accounting for a change in a position of the portion of the subject's body between acquisition of the additional image and acquisition of the sequence of radiographic images.

In some applications, the method further includes, using the computer processor, determining an extent of foreshortening of respective portions of the endoluminal path of the device through the lumen, by analyzing the plurality of radiographic images.

In some applications, the lumen includes a lumen that undergoes cyclical motion as a result of a physiological cycle of the subject, and defining the set of locations includes identifying a set of locations at which the one or more radiopaque portions of the endoluminal device were imaged at a given phase of the subject's physiological cycle.

In some applications, defining the set of locations includes:

identifying a sub-set of the identified locations at which the one or more radiopaque portions of the endoluminal device were imaged, such that each member of the sub-set of the identified locations is disposed within a given distance from at least one other member of the sub-set of the identified locations; and defining the sub-set of the identified locations as the set of locations at which the one or more radiopaque portions of the endoluminal device were disposed during the movement of the endoluminal device through the lumen.

In some applications, the method further includes, using the computer processor:
receiving an image of the lumen in which the lumen is visible;
receiving an indication of a center-line of the lumen within the received image of the lumen; and
registering respective locations along the estimated endoluminal path of the device through the lumen to respective locations along the center-line of the lumen within the received image of the lumen.

In some applications,
the method further comprises, using the computer processor:
receiving an image of the lumen in which the lumen is visible; and
receiving an indication of a center-line of the lumen within the received image of the lumen, and
estimating the endoluminal path of the device through the lumen comprises estimating the endoluminal path of the device through the lumen using the set of locations in combination with the lumen center-line.

In some applications, the endoluminal device includes an endoluminal data-acquisition device configured to acquire a plurality of endoluminal data sets at respective locations along the lumen, the method further including registering respective endoluminal data sets to respective locations along the estimated endoluminal path of the device through the lumen.

In some applications, the method further includes, using the computer processor:
receiving an image of the lumen in which the lumen is visible; and
registering respective endoluminal data sets to respective locations along the lumen in the received image, based upon the registering of the respective endoluminal data sets to the respective locations along the estimated endoluminal path of the device through the lumen.

In some applications, the method further includes determining diameters of the lumen at respective locations along the estimated endoluminal path of the device through the lumen, based upon the registering of the respective endoluminal data sets to the respective locations along the estimated endoluminal path of the device through the lumen.

In some applications, the method further includes identifying a location of a lesion along the estimated endoluminal path of the device through the lumen, based upon the determined diameters of the lumen.

In some applications, defining the set of locations includes generating a combined image in which the identified locations form an integrated set of locations, by overlaying, upon each other, images in which the radiopaque portions of the endoluminal device have been identified.

In some applications, defining the set of locations further includes identifying that one or more locations within the combined image at which radiopaque features were imaged within the radiographic image sequence do not correspond to locations at which the radiopaque portions of the endoluminal device were disposed, and excluding the one or more locations from the set of locations.

In some applications, estimating the endoluminal path of the device through the lumen includes identifying a curve that defines the set of locations within the combined image and estimating that the endoluminal path of the device through the lumen was along the identified curve.

In some applications, the method further includes estimating a location of a center-line of the lumen based upon the estimated endoluminal path of the device.

In some applications, estimating the location of the center-line of the lumen includes:
using the computer processor, receiving an image of the lumen in which the lumen is visible; and
estimating the location of the center-line with respect to the received image of the lumen, using the estimated endoluminal path of the device as an input for estimating the location of the center-line.

In some applications, the endoluminal device includes an endoluminal data-acquisition device configured to acquire a plurality of endoluminal data sets at respective locations along the lumen, the method further including registering respective endoluminal data sets to respective locations along the estimated center-line.

In some applications, registering respective endoluminal data sets to respective locations along the estimated center-line includes directly registering respective endoluminal data sets to respective locations along the estimated center-line.

In some applications, registering respective endoluminal data sets to respective locations along the estimated center-line includes:
registering respective endoluminal data sets to respective locations along the estimated endoluminal path of the device; and
registering the estimated endoluminal path to the estimated center-line.

There is further provided, in accordance with some applications of the present invention, apparatus including:
an endoluminal device that comprises one or more radiopaque portions and that is configured to move through a lumen of a subject;
a radiographic imaging device configured to acquire a sequence of radiographic images of a portion of the subject's body in which the lumen is disposed, during movement of the endoluminal device through the lumen;
an output device; and
at least one computer processor configured to:
identify locations at which the one or more radiopaque portions of the endoluminal device were imaged during the movement of the endoluminal device through the lumen, by analyzing the sequence of radiographic images;
define a set of locations at which the one or more radiopaque portions of the endoluminal device were disposed during the movement of the endoluminal device through the lumen, based upon the identified locations;
estimate an endoluminal path of the device through the lumen based upon the set of locations; and
generate an output on the output device.

In some applications, the lumen includes a lumen of the subject that undergoes motion, and the computer processor is configured to estimate an endoluminal path of the device through the lumen that undergoes motion.

In some applications, the computer processor is configured, based upon the estimated endoluminal path, to register a current position of the portion of the subject's body to an additional image of the portion of the subject's body, by accounting for a change in a position of the portion of the subject's body between acquisition of the additional image and acquisition of the sequence of radiographic images.

In some applications, the computer processor is configured to determine an extent of foreshortening of respective portions of the endoluminal path of the device through the lumen, by analyzing the plurality of radiographic images.

In some applications, the lumen includes a lumen that undergoes cyclical motion as a result of a physiological cycle of the subject, and the computer processor is configured to define the set of locations by identifying a set of locations at which the one or more radiopaque portions of the endoluminal device were imaged at a given phase of the subject's physiological cycle.

In some applications, the computer processor is configured to define the set of locations by:
   identifying a sub-set of the identified locations at which the one or more radiopaque portions of the endoluminal device were imaged, such that each member of the sub-set of identified locations is disposed within a given distance from at least one other member of the sub-set of the identified locations, and
   defining the sub-set of the identified locations as the set of locations at which the one or more radiopaque portions of the endoluminal device were disposed during the movement of the endoluminal device through the lumen.

In some applications, the computer processor is configured to:
   receive an image of the lumen in which the lumen is visible;
   receive an indication of a center-line of the lumen within the received image of the lumen; and
   register respective locations along the estimated endoluminal path of the device through the lumen to respective locations along the center-line of the lumen within the received image of the lumen.

In some applications, the computer processor is configured:
   to receive an image of the lumen in which the lumen is visible; and
   to receive an indication of a center-line of the lumen within the received image of the lumen,
   to estimate the endoluminal path of the device through the lumen by estimating the endoluminal path of the device through the lumen using the set of locations in combination with the lumen center-line.

In some applications, the endoluminal device includes an endoluminal data-acquisition device configured to acquire a plurality of endoluminal data sets at respective locations along the lumen, and the computer processor is configured to register respective endoluminal data sets to respective locations along the estimated endoluminal path of the device through the lumen.

In some applications, the computer processor is configured to:
   receive an image of the lumen in which the lumen is visible; and
   register respective endoluminal data sets to respective locations along the lumen in the received image, based upon the registering of the respective endoluminal data sets to the respective locations along the estimated endoluminal path of the device through the lumen.

In some applications, the computer processor is configured to determine diameters of the lumen at respective locations along the estimated endoluminal path of the device through the lumen, based upon the registering of the respective endoluminal data sets to the respective locations along the estimated endoluminal path of the device through the lumen.

In some applications, the computer processor is configured to identify a location of a lesion along the estimated endoluminal path of the device through the lumen, based upon the determined diameters of the lumen.

In some applications, the computer processor is configured to define the set of locations by generating a combined image in which the identified locations form an integrated set of locations, by overlaying, upon each other, images in which the radiopaque portions of the endoluminal device have been identified.

In some applications, the computer processor is configured to define the set of locations by:
   identifying that one or more locations within the combined image at which radiopaque features were imaged within the radiographic image sequence do not correspond to locations at which the radiopaque portions of the endoluminal device were disposed, and
   excluding the one or more locations from the set of locations.

In some applications, the computer processor is configured to estimate the endoluminal path of the device through the lumen by identifying a curve that defines the set of locations within the combined image and estimating that the endoluminal path of the device through the lumen was along the identified curve.

In some applications, the computer processor is configured to estimate a location of a center-line of the lumen based upon the estimated endoluminal path of the device.

In some applications, the computer processor is configured to estimate the location of the center-line of the lumen by:
   receiving an image of the lumen in which the lumen is visible; and
   estimating the location of the center-line with respect to the received image of the lumen, using the estimated endoluminal path of the device as an input for estimating the location of the center-line.

There is further provided, in accordance with some applications of the present invention, a computer software product, for use with an endoluminal device that includes one or more radiopaque portions and that moves through a lumen of a subject, and a radiographic imaging device, configured to acquire a sequence of radiographic images of a portion of the subject's body in which the lumen is disposed, during movement of the endoluminal device through the lumen, the computer software product including a non-transitory computer-readable medium in which program instructions are stored, which instructions, when read by a computer cause the computer to perform the steps of: identifying locations at which the one or more radiopaque portions of the endoluminal device were imaged during the movement of the endoluminal device through the lumen, by analyzing the sequence of radiographic images; defining a set of locations at which the one or more radiopaque portions of the endoluminal device were disposed during the movement of the endoluminal device through the lumen, based upon the identified locations; estimating an endoluminal path of the device through the lumen based upon the set of locations; and, generating an output on an output device.

There is further provided, in accordance with some applications of the present invention, a method including:
   while an endoluminal data-acquisition device moves along a portion of a lumen:
      acquiring a plurality of endoluminal data sets from respective locations along the lumen, using the endoluminal data-acquisition device; and
      acquiring a sequence of extraluminal images of the endoluminal device inside the lumen, using an extraluminal imaging device;

using at least one computer processor, coregistering respective endoluminal data sets to respective locations along a path of the lumen, without requiring the user to input, to the computer processor, an indication of a shape of the path of the lumen.

The scope of the present application includes combining the apparatus and methods described herein with apparatus and methods described in any one of the following applications, all of which are incorporated herein by reference:

International Application PCT/IL2008/000316 to Iddan (published as WO 08/107905), filed Mar. 9, 2008, entitled "Imaging and tools for use with moving organs."

U.S. patent application Ser. No. 12/075,252 to Iddan (published as US 2008/0221440), filed Mar. 10, 2008, entitled "Imaging and tools for use with moving organs;"

International Application PCT/IL2009/000610 to Iddan (published as WO 09/153794), filed Jun. 18, 2009, entitled "Stepwise advancement of a medical tool;"

U.S. patent application Ser. No. 12/487,315 to Iddan (issued as U.S. Pat. No. 8,700,130), filed Jun. 18, 2009, entitled "Stepwise advancement of a medical tool;"

U.S. patent application Ser. No. 12/666,879 to Steinberg (issued as U.S. Pat. No. 8,781,193), which is the US national phase of PCT Application No. PCT/IL2009/001089 to Cohen (published as WO 10/058398), filed Nov. 18, 2009, entitled "Image processing and tool actuation for medical procedures;"

U.S. patent application Ser. No. 12/781,366 to Cohen (published as US 2010/0222671), filed May 17, 2010, entitled "Identification and presentation of device-to-vessel relative motion;"

International Patent Application PCT/IL2011/000391 to Cohen (published as WO 11/145094), filed May 17, 2011, entitled "Identification and presentation of device-to-vessel relative motion;"

U.S. Ser. No. 13/228,229 to Tolkowsky (published as US 2012/0004537), filed Sep. 8, 2011, which is a continuation of International Application No. PCT/IL2011/000612 to Tolkowsky (published as WO 12/014212), filed 28 Jul. 2011 entitled "Co-use of endoluminal data and extraluminal imaging;"

U.S. patent application Ser. No. 14/128,243 to Barzelay (published as US 2014/0140597), which is the US national phase of International Patent Application PCT/IL2012/000246 (published as WO 12/176191), filed Jun. 21, 2012, entitled "Luminal background cleaning;"

U.S. patent application Ser. No. 14/097,922 to Steinberg (published as US 2014/0094691), filed Dec. 5, 2013, entitled "Co-use of endoluminal data and extraluminal imaging," which is a continuation of International Application PCT/IL2013/050438 (published as WO 13/175472) to Steinberg, filed May 21, 2013, entitled "Co-use of endoluminal data and extraluminal imaging;"

U.S. patent application Ser. No. 14/142,082 to Tolkowsky (published as US 2014/0121513), filed Dec. 27, 2013, entitled "Determining a characteristic of a lumen by measuring velocity of a contrast agent," which is a continuation of International Application PCT/IL2013/050549 (published as WO 14/002095) to Tolkowsky, filed Jun. 26, 2013, entitled "Flow-related image processing in luminal organs;"

International Patent Application PCT/IL2015/050372 to Klaiman (published as WO 15/155770), filed Apr. 2, 2015, entitled "Image analysis in the presence of a medical device," which claims priority from U.S. Provisional Patent Application 61/977,891 to Klaiman, filed Apr. 10, 2014, entitled "Image analysis in the presence of a medical device;" and International Patent Application PCT/IL2015/050509 to Klaiman (published as WO 15/173821), filed May 13, 2015, entitled "Object identification," which claims priority from U.S. Provisional Patent Application 61/993,123 to Klaiman, filed May 14, 2014, entitled "Image analysis in the presence of a medical device."

The invention claimed is:

1. An apparatus comprising:
a computer processor configured for communication with at least one extraluminal image-acquisition device, an endoluminal device, and a display, wherein the computer processor is configured to:
receive, from the at least one extraluminal image-acquisition device, a plurality of first extraluminal images of a body lumen during movement of the endoluminal device through the body lumen and obtained without a contrast agent within the body lumen;
determine, based on the plurality of first extraluminal images, a path of the endoluminal device through the body lumen using a centerline of a shape formed to include only a plurality of locations of a radiopaque portion of the endoluminal device during the movement of the endoluminal device;
receive, from the at least one extraluminal image-acquisition device, a second extraluminal image of the body lumen obtained with the contrast agent within the body lumen;
determine, based on the second extraluminal image, a centerline of the body lumen; and
provide, on the display, an output comprising the path of the endoluminal device and the centerline of the body lumen, wherein the path of the endoluminal device and the centerline of the body lumen are displayed simultaneously.

2. The apparatus of claim 1, wherein the output further comprises the second extraluminal image, wherein the path of the endoluminal device and the centerline of the body lumen are overlaid on the second extraluminal image.

3. The apparatus of claim 1, wherein the computer processor is configured to determine the centerline of the body lumen based on a user input indicating at least one of how the centerline of the body lumen is shaped or where the centerline of the body lumen is located.

4. The apparatus of claim 1, wherein the computer processor is configured to determine the centerline of the body lumen automatically without a user input indicating at least one of how the centerline of the body lumen is shaped or where the centerline of the body lumen is located.

5. The apparatus of claim 4, wherein the computer processor is configured to determine the centerline of the body lumen based on the path of the endoluminal device.

6. The apparatus according to claim 1,
wherein the body lumen is a body lumen that undergoes motion and
wherein the computer processor is configured to determine the path of the endoluminal device through the body lumen that undergoes motion.

7. The apparatus according to claim 6,
wherein the body lumen is a body lumen that undergoes cyclical motion as a result of a physiological cycle, and wherein the computer processor is configured to determine the path of the endoluminal device through the body lumen that undergoes cyclical motion.

8. The apparatus according to claim 1, wherein the computer processor is configured, based upon the path of the endoluminal device, to register a current position of a portion of the body lumen to an additional image of the portion of the body lumen, by accounting for a change in a position of the portion of the body lumen between acquisition of the additional image and acquisition of the plurality of first extraluminal images.

9. The apparatus according to claim 1, wherein the computer processor is configured to determine an extent of foreshortening of respective portions of the path of the endoluminal device through the body lumen, by analyzing the plurality of first extraluminal images.

10. The apparatus according to claim 1, wherein the computer processor is configured to register respective locations along the path of the endoluminal device to respective locations along the centerline of the body lumen.

11. The apparatus according to claim 1, wherein the body lumen is visible in the second extraluminal image.

12. The apparatus according to claim 1,
wherein the computer processor is configured for communication with an endoluminal data-acquisition device and wherein the computer processor is configured to:
   acquire, from the endoluminal data-acquisition device, endoluminal data at respective locations along the body lumen, and
   register the endoluminal data to respective locations along the path of the endoluminal device through the body lumen.

13. The apparatus according to claim 12,
wherein the body lumen is visible in the second extraluminal image, and
wherein the computer processor is configured to register the endoluminal data to the respective locations along the body lumen in the second extraluminal image based upon the registering of the endoluminal data to the respective locations along the path of the endoluminal device through the body lumen.

14. The apparatus according to claim 12, wherein the computer processor is configured to determine diameters of the body lumen at the respective locations along the path of the endoluminal device through the body lumen, based upon the registering of the endoluminal data to the respective locations along the path of the endoluminal device through the body lumen.

15. The apparatus according to claim 14, wherein the computer processor is configured to identify a location of a lesion along the path of the endoluminal device through the body lumen, based upon the determined diameters of the body lumen.

* * * * *